(12) United States Patent
Landis

(10) Patent No.: US 7,490,359 B2
(45) Date of Patent: Feb. 17, 2009

(54) LIGHTWEIGHT VENTILATED FACE SHIELD FRAME

(75) Inventor: Timothy J. Landis, Roseville, CA (US)

(73) Assignee: OP-D-OP, Inc., Roseville, CA (US)

( * ) Notice: Subject to any disclaimer, the term of this patent is extended or adjusted under 35 U.S.C. 154(b) by 0 days.

(21) Appl. No.: 11/265,549

(22) Filed: Nov. 1, 2005

(65) Prior Publication Data

US 2006/0112474 A1 Jun. 1, 2006

Related U.S. Application Data

(63) Continuation of application No. PCT/US2004/013763, filed on May 3, 2004.

(60) Provisional application No. 60/467,791, filed on May 2, 2003.

(51) Int. Cl.
 *A41D 13/00* (2006.01)

(52) U.S. Cl. .................... 2/9; 2/206; 2/427; 128/857

(58) Field of Classification Search ............ 2/9, 2/427, 15, 11, 12, 206, 432, 429, 436; 128/857, 128/858

See application file for complete search history.

(56) References Cited

U.S. PATENT DOCUMENTS

| | | | | |
|---|---|---|---|---|
| 2,610,323 A | * | 9/1952 | Oliver | 2/8.1 |
| 2,729,820 A | * | 1/1956 | Anderson | 2/8.1 |
| 2,731,637 A | | 1/1956 | Kaplan et al. | |
| 2,758,307 A | * | 8/1956 | Treiber | 2/9 |
| 2,829,374 A | * | 4/1958 | Malcom, Jr. | 2/9 |
| 2,881,443 A | | 4/1959 | Barker | |
| 3,214,767 A | * | 11/1965 | Weber | 2/9 |
| 3,214,768 A | * | 11/1965 | Bohner | 2/10 |
| 3,763,495 A | * | 10/1973 | De Angelis | 2/8.1 |
| 3,868,727 A | * | 3/1975 | Paschall | 2/8.5 |
| 4,097,930 A | * | 7/1978 | Bay | 2/10 |
| 4,701,965 A | * | 10/1987 | Landis | 2/428 |
| 4,850,049 A | | 7/1989 | Landis et al. | |
| 4,852,186 A | | 8/1989 | Landis | |
| 4,864,653 A | | 9/1989 | Landis | |
| 4,920,576 A | | 5/1990 | Landis | |

(Continued)

FOREIGN PATENT DOCUMENTS

EP 0242988 A2 10/1987

(Continued)

*Primary Examiner*—Gary L Welch
*Assistant Examiner*—Nathan E Durham
(74) *Attorney, Agent, or Firm*—John P. O'Banion

(57) ABSTRACT

A lightweight face shield which protects the face of the wearer from debris and/or hazardous materials, such as biological materials, and is particularly well suited for medical and dental applications. The face shield utilizes a two-piece tiered structure with a preferably canted retention frame joined through an inclined structure member to a shield frame member below which is retained a transparent shield, and above which a minishield. The shield frame member is retained forward of the retention frame member so as to retain the peripheral portions of the shield separated from the face of the user, providing improved ventilation and reduced fogging of the transparent shield. A trampoline style support arm is described that provides solid retention, compliant comfort, and reduced material requirements. Optional locking hinge assemblies for the support arms and a nose bridge are also described.

40 Claims, 13 Drawing Sheets

U.S. PATENT DOCUMENTS

| | | | |
|---|---|---|---|
| 4,945,573 A | 8/1990 | Landis | |
| 4,964,171 A | 10/1990 | Landis | |
| 4,965,887 A * | 10/1990 | Paoluccio et al. | 2/9 |
| 4,986,282 A * | 1/1991 | Stackhouse et al. | 128/857 |
| 5,220,689 A * | 6/1993 | Miller | 2/12 |
| 5,390,369 A | 2/1995 | Tubin | |
| 5,469,229 A * | 11/1995 | Greenbaum | 351/44 |
| 5,471,679 A | 12/1995 | Paoluccio | |
| 5,503,497 A | 4/1996 | Dudley et al. | |
| 5,544,361 A * | 8/1996 | Fine et al. | 2/10 |
| D375,583 S | 11/1996 | Landis et al. | |
| 5,600,870 A | 2/1997 | Fields et al. | |
| 5,608,917 A | 3/1997 | Landis et al. | |
| 5,615,414 A | 4/1997 | Landis | |
| 5,647,060 A | 7/1997 | Lee | |
| 5,673,431 A * | 10/1997 | Batty | 2/9 |
| 5,682,608 A | 11/1997 | Landis | |
| 5,692,522 A | 12/1997 | Landis | |
| 5,765,223 A * | 6/1998 | McCausland | 2/9 |
| 5,862,530 A * | 1/1999 | Shillington | 2/439 |
| 5,933,862 A | 8/1999 | Landis | |
| 6,016,808 A | 1/2000 | Landis | |
| 6,056,400 A * | 5/2000 | Knepp | 351/155 |
| 6,278,788 B1 | 8/2001 | Landis et al. | |
| 6,481,025 B2 * | 11/2002 | Hill | 2/453 |
| 6,490,757 B2 | 12/2002 | Landis et al. | |
| 6,564,804 B2 * | 5/2003 | Salatka et al. | 128/857 |
| 2002/0023286 A1 * | 2/2002 | Landis et al. | 2/175.2 |
| 2002/0029399 A1 * | 3/2002 | Hill | 2/13 |
| 2002/0134390 A1 | 9/2002 | Salatka et al. | |

FOREIGN PATENT DOCUMENTS

| | | |
|---|---|---|
| FR | 1024440 A | 4/1953 |
| WO | WO 2004098715 A2 * | 11/2004 |

\* cited by examiner

LIGHTWEIGHT VENTILATED FACE SHIELD FRAME

CROSS-REFERENCE TO RELATED APPLICATIONS

This application claims priority to, and is a 35 U.S.C. § 111(a) continuation of, co-pending PCT international application serial number PCT/US2004/013763, filed on May 3, 2004, which designates the U.S., which claims priority to U.S. provisional application Ser. No. 60/467,791, filed on May 2, 2003, each of which is incorporated herein by reference in its entirety.

This application is also related to PCT International Publication Nos. WO 2004/098715 A2 and WO 2004/098715 A3, each of which is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

The present invention pertains to head-mounted face shield frames and more particularly to a light weight, ventilated, frame having an open tiered structure that provides rigidity while reducing frame weight.

2. Description of Related Art

In a number of industries, the use of a face shield provides protection for the eyes and face of the wearer from debris or biological materials. Increasingly, face shields are being utilized for preventing infections that can occur as a result of bodily fluid splattering that can arise within a number of occupations. A number of factors affect the acceptance of a face shield design, including comfort, ventilation, weight, ability to be securely retained in position, cost, and aesthetic considerations. The need for secure positioning and ventilation, which increases comfort while reducing the possibility of fogging, can be critical performance factors, especially in situations in which the face shield needs to be worn for extended periods of time.

The type of face shields being described herein attach to the head of a user with support arms that extend rearwardly from a frame upon which is retained a transparent face shield that affords debris and splatter protection to the wearer. To provide a secure and comfortable fit, the support arms are preferably configured to have sufficient horizontal stiffness to support a transparent shield which is separated sufficiently far from the face, without causing discomfort to the user.

A number of examples of practical face shields exist. Examples of face shields which are being increasingly utilized in a number of industries may be found in the following United States Patents by Timothy J. Landis, including U.S. Pat. No. 4,852,186 of Aug. 1, 1989 entitled "Combined Visor and Protective Shield", U.S. Pat. No. 4,864,653 of Sep. 12, 1989 entitled "Protective Shield and Visor Supporting Same", U.S. Pat. No. 4,964,171 of Oct. 23, 1990 entitled "Protective Shield and Visor", Design Pat. No. 375,583 of Nov. 12, 1996 entitled "Disposable Face Shield", U.S. Pat. No. 5,692,522 of Dec. 2, 1997 entitled "Face Shield Apparatus", and U.S. Pat. No. 6,016,808 of Jan. 25, 2000 entitled "Face Shield Frame Apparatus". The above face shields provide numerous benefits and are included herein by reference. It will be appreciated, however, that the growing market for face shields is always in search of improved face shield designs that provide increasing utility, comfort, and style while reducing material requirements and manufacturing costs.

Therefore, a need exists for a lightweight face shield frame that can be maintained securely in position while providing ample ventilation, and which can be manufactured at low cost and stored compactly. The present invention satisfies those needs, as well as others, and overcomes the deficiencies of previously developed face shield designs.

BRIEF SUMMARY OF THE INVENTION

The present invention describes a face shield apparatus and method of forming a lightweight tiered face shield frame with enhanced retention, ventilation and comfort while designed to allow manufacturing it in stylish configurations. The open design of the frame within the present invention provides necessary rigidity while reducing material weight. The tiered design of the present invention is stylish and readily manufactured, while utilizing only small amounts of material.

The present face shield apparatus comprises a two piece frame with a retention frame member interconnected through an inclined support structure with a shield frame member. A transparent shield is attached to and extends below the shield frame member, while a minishield member is retained above the shield frame member to control the amount of shading provided over the eyes of the wearer while providing debris protection. The optional minishield may be attached to the face shield frame as received by a customer, or may be user installable, depending on the need. The tiered arrangement of the face shield frame allows retaining the transparent shield in separation from both the front and sides of the wearer's face with a view towards increasing ventilation and reducing the opportunity for fogging of the transparent shield.

The retention frame of the invention provides sufficient structural rigidity for being retained securely on the head, and with flexure that is distributed about the retention frame to properly accommodate varying head sizes. Points of contact between the retention frame and the head of the wearer is preferably limited to a region at the front interior of the retention frame and portions of the support arms which meet the head behind the location of the ears.

The shield frame member is configured with a radius of curvature that exceeds that of the retention frame, such as from one half inch to about two inches, to provide separation between the transparent shield and the face of the wearer. Although it should not be construed that the retention frame member and shield frame member need have a circular profile, as they may be fabricated according to the present invention in any shape that may sufficiently conform to the head. The retention frame member is joined to the shield frame member at a position above the shield frame member (relative positioning described during use). The central arcuate section of the retention frame extends generally tangentially into support arms that extend therefrom for applying pressure at contact points along the side of the head. These points of contact on the ends of the support arms are preferably configured to make secure contact on the head of the wearer, such as by offering a small surface area of contact while maintaining sufficient structural rigidity.

The ends of the support arms are preferably webbed, and may be configured as either two or three dimensional structures. The webbed portion on the support arms distributes retention pressure, having open areas of at least one quarter square inch in size, although more preferably at least one half square inch. Utilizing three dimensional distributed structures allows proffering narrow elements in contact with the head which are supported by additional structures not in contact with the head of the wearer. This preferred support arm is a ventilated trampoline style structure, having an exterior support element that supports a flexible interior element. This trampoline structure is capable of supporting narrow yet compliant contact areas on the head while requiring minimal amounts of material for fabrication.

The retention frame can be manufactured with removable support arms to simplify storage and shipping requirements. An articulating mechanism, such as locking hinge assemblies, may be incorporated within the support arms joined to the retention frame so that the retention frame may be adjusted for a proper fit on different head sizes and shapes. By way of example, locking hinge assemblies allow adjusting the position of the support arms to suit users having different head sizes and shapes. The hinge assemblies may be either integrated within the retention frame member, wherein the support arms connect to the opposing side of the hinge, or they may be integrated within the support arm itself, wherein a remaining portion of the support arm extending from the hinge assembly may be adjusted. A locking hinge assembly with a push button disengagement mechanism is a preferred form of locking hinge assembly.

The face shield unit may be configured as a single piece construction, or from separate elements that are interconnected prior to use. By way of example, the retention frame member can be separated from the inclined support members attached to the shield frame and transparent shield. Portions of the frame members are preferably configured with open web structures to reduce the material weight while maintaining structural rigidity.

An optional nose bridge member may be joined to the retention frame member for supporting a portion of the weight of the face shield on the bridge of the nose. The nose bridge may be configured as a permanently mounted element, or more preferably as an element that may be joined to the retention frame member prior to use, at the discretion of the wearer.

The face shield frames of the present invention can be fitted with a number of optional elements without departing from the teachings herein. By way of example, the interior of the retention frame and extended support arms may optionally include padding or other pressure distribution devices, in particular near the distal ends of the support arms. One form of pads that are preferably utilized are flow cells, wherein a compliant exterior container is filled with a fluid material such as liquid, gas, or preferably a gel material.

It is contemplated that typically the face shields of the present invention will be made available with a minishield attached to a shield frame member and optionally the transparent shield preattached, wherein the user need only connect the shield frame to the retention frame prior to use. Attaching the transparent shield to the shield frame at the point of use can provide a significant reduction in storage volume. Furthermore the minishield and even the retention frame may be assembled together at the point of use to further reduce storage requirements. These user-assembled face shields could be considered "kits", wherein the user connects the elements of retention frame, support arms, face shield frame, transparent shield, minishield, and optional nose bridge. It will be appreciated that one or more of these elements may be optional or preassembled.

The present face shield invention may be considered to generally comprise a retention frame member for being secured to the head of a wearer and a means for retaining a transparent shield member separated from the retention frame member. The means for retaining the transparent shield may also retain a minishield member substantially adjoining the upper portion of the transparent shield member. The separation between the retention frame and means providing ventilation space to prevent fogging of the transparent shield during use. Preferably this space is at least three quarters of an inch (¾ inch) to approximately three or four inches (3–4 inches) in front of the retention frame. This spacing being preferably sufficient for retaining a minishield while maintaining a ventilation gap through which air may flow past the face of the wearer and exit between the minishield and the retention frame.

The means of retaining a transparent shield may be implemented as a shield frame member, preferably having an arcuate shape with a radius exceeding the retention frame member. One or more support elements, such as an inclined support which preferably attaches the shield frame member to the retention frame member, and may be separate or preferably permanently joined to one of the frame members, such as the shield frame member. The shield frame is configured with fastening means for engaging a transparent shield, such as tabs or similar protrusions that can engage apertures or recesses in the transparent shield. The transparent shield preferably comprises a transparent polymeric material, such as removed (i.e. cut from) a sheet of transparent polymeric material. The transparent shield may comprise material selected from the group of polymeric materials consisting of polystyrene, acrylic, polyethylene, terephthalate, polycarbonate, or equivalent polymeric material.

An aspect of the invention is providing a secure and comfortable face shield that may be manufactured in stylish configurations.

Another aspect of the invention is providing a face shield which is retained securely on the head thereby reducing the need for repositioning or adjustment while in use.

Another aspect of the invention is providing a face shield frame adapted for the attachment of a transparent shield member which can be performed manually, such as by end-users.

Another aspect of the invention is providing a well ventilated face shield in which air can freely flow between the shield frame with attached transparent shield and the retention member which joins the face shield to the wearer.

Another aspect of the invention is providing a face shield frame upon which a minishield may be mounted.

Another aspect of the invention is providing a face shield upon which the transparent shield is retained away from the face of the wearer including the peripheral areas so as to encourage airflow and reduce fogging.

Another aspect of the invention is providing a face shield that stores compactly and is assembled at the point of use.

Another aspect of the invention is providing a face shield formed with two interconnected frame members.

Another aspect of the invention is providing a face shield frame having articulated support arms for adjusting the fit for different head sizes and shapes.

Another aspect of the invention is providing a face shield frame having removable support arms to facilitate shipment and storage.

Another aspect of the invention is providing a face shield frame having ventilated support arm ends which contact the head of the wearer for applying retention pressure.

Another aspect of the invention is providing a face shield frame in which the support arm ends provide a three-dimensional ventilated structure that applies contact forces to small areas of the head while having additional support structures that hold the shape of the contact structures but which are not in contact with the head.

Another aspect of the invention is providing a face shield frame whose support arms have a trampoline structure with a substantially stiff exterior frame which supports both ends of a flexible webbing.

Another aspect of the invention is providing a face shield with an optional nose bridge assembly for supporting a portion of the load, and which may be used at the discretion of the user.

Further aspects and advantages of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Referring more specifically to the drawings, for illustrative purposes the present invention is embodied in the apparatus generally shown in FIG. 1 through FIG. 15. It will be appreciated that the apparatus may vary as to configuration and as to details of the parts, and that the method may vary as to the specific steps and sequence, without departing from the basic concepts as disclosed herein.

Figure 1:
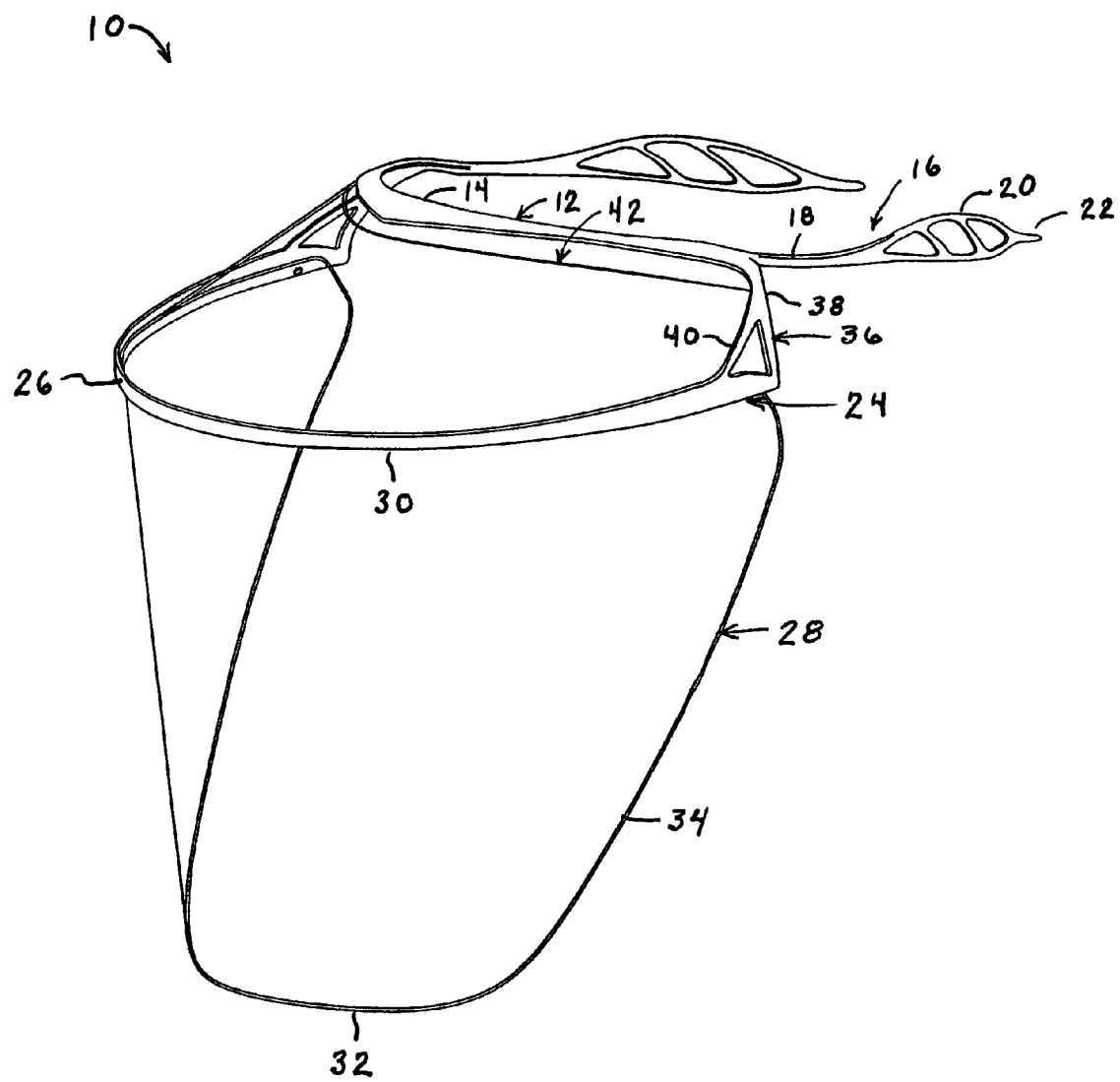
FIG. 1 is a perspective view of a face shield according to an embodiment of the present invention and shown with an upper tier retention frame member joined to a lower tier shield frame member to which are joined a transparent face shield and an optional semitransparent minishield.
Figure 2:
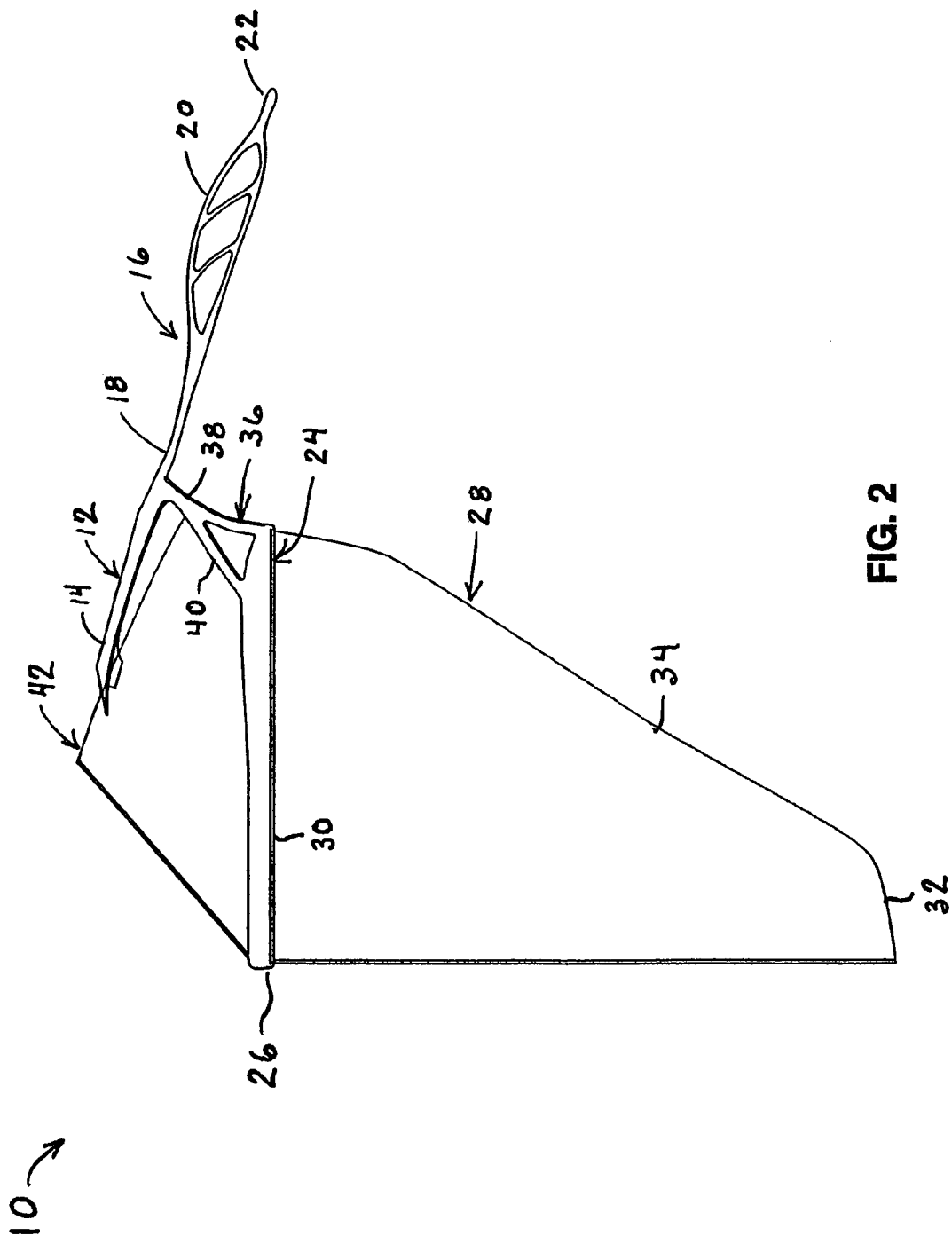
FIG. 2 is side view of the face shield shown in FIG. 1.

FIG. 1 through FIG. 5 exemplify a two tier face shield 10 according to an embodiment of the present invention. FIG. 1 and FIG. 2 provide views of the assembled face shield 10 comprising upper retention frame member 12 having a central arcuate section 14 which extends rearwardly to support arms 16. The arc of curvature of the shield frame member preferably has a radius which exceeds that of the retention frame member, such as by a minimum of approximately one half inch, wherein the shield member is retained away from the periphery of the face of the wearer by at least about one-half inch on either side, wherein air may circulate to keep the face of the wearer cool and dry while reducing the opportunity of the face shield to fog up. More preferably, the radius of curvature of the shield frame member exceeds that of the retention frame member by at least approximately three quarters of an inch to approximately three inches.

To increase comfort while maintaining positive retention, the retention frame member is preferably configured for positioning on the head of the wearer at an angle so that the front of the retention frame member is raised above the distal end of the support arms, such as a minimum of one quarter inch (¼ inch), or more preferably from about one half inch (½ inch) to about one and one half inches (1½ inches). This is preferably measured from the center of arc on the retention member in relation to the center of the distal end of the support arm.

The material of the frame members preferably comprises a thermoplastic material which may be utilized with conventional molding processes. Each support arm 16 extending from arcuate section 14 has a proximal section 18. A webbed region 20 is shown near distal end 22. The material in the webbed region is configured for applying pressure over narrow distributed areas, preferably less than approximately one quarter inch wide or more preferably less than one eighth inch wide, on the side of the head of the wearer to assure secure retention, in which the face shield is prevented from sliding about. To distribute contact pressure in this manner, each support arm is preferably adapted with an enlarged section 20, for example, a webbed region in which one or more perimeters of material surround one or more open regions. Preferably, a minimum of approximately one half square inch, and more preferably an open area from approximately one square inch to approximately three square inches, are provided within enlarged section 20 to increase ventilation and distribute pressure.

A lower shield frame member 24 preferably has a central arcuate section 26 to which is attached a transparent shield 28. It should also be appreciated that shield frame member 24 may be manufactured according to different geometric configurations, oval, rectangular, and so forth, without departing from the teachings of the present invention. The transparent shield may be attached permanently, semi-permanently, or temporarily to shield frame member 24. To allow packaging the face shields at a higher density (more compactly), such as nesting of the face shields, the lower shield frame member 24 can be designed with a fastener that can be manually activated, such as after receipt by an end-user, to engage the transparent face shield. Examples of the manually activated engagement means include snap-in connectors, tabs, pins, fasteners, contact forms of adhesives (i.e. peeling a covering from adhesive area and applying), and so forth. By way of example, the shield frame may include a first set of connectors which are configured to engage a mating set of connectors on the transparent shield. These connectors preferably comprise protrusions extending from the shield frame that engage and lock into apertures upon the transparent shield.

Shield frame 24 is preferably curved and positioned in separation from the retention frame so as to provide clearance between the transparent shield and the face of the wearer. It will be appreciated that the present tiered design allows clearance to be incorporated not only at the front of the face shield but also along the periphery of the face shield to increase ventilation and reduce fogging.

Transparent shield member 28 has an upper edge 30, lower edge 32, and side edges 34, and preferably comprises a transparent flexible plastic material, such as cut out from a sheet of plastic material. By way of example and not limitation, preferred plastic materials include polystyrene, acrylic, polyethylene, terephthalate, polycarbonate, equivalent polymeric materials, or similar.

The retention frame member 12 is connected to the shield frame member 24 by at least a pair of support members 36, preferably inclined supports, each having an upper attachment structure 38 and lower attachment structure 40, one or more of which preferably includes a webbed area to increase support. These inclined support members 36 preferably comprise more than one structural element to distribute the weight of the shield frame member and transparent shield, along with any forces that may be applied by the wearer when the face shield is put on, taken off, or subject to occasional loads during use (i.e. being bumped). Preferably, inclined support 36 comprises a webbed region having a perimeter that surrounds a section which includes at least one open area having a minimum of approximately one quarter square inch, and more preferably between approximately one half square inch to approximately one square inch. By way of example, the embodiment illustrates inclined support 36 connecting at a single location to the retention frame member 12 and forking into two supports prior to connection to the shield frame member 24.

Optionally joined above the shield frame member 24, is a minishield 42 which may comprise any shaded, semi-transparent to opaque material, for shading the eyes and protecting the upper face and head from flying material debris. It should be appreciated that ventilation space exists above the minishield and that the minishield may be manufactured of different shapes and widths to provide a desired amount of shading and ventilation. Shield frame member 24 may be adapted using any convenient means to receive minishield 42 on the exterior or interior surfaces of arcuate section 26. By way of example minishield 42 may be attached such as with tape, locking pins, hook-and-loop style fasteners, or other convenient permanent or temporary mounting methods. Alternatively, minishield 42 may be permanently installed along with the transparent shield 28, such as using adhesives, thermal bonding techniques, permanent fasteners, and combinations thereof.

Figure 3:
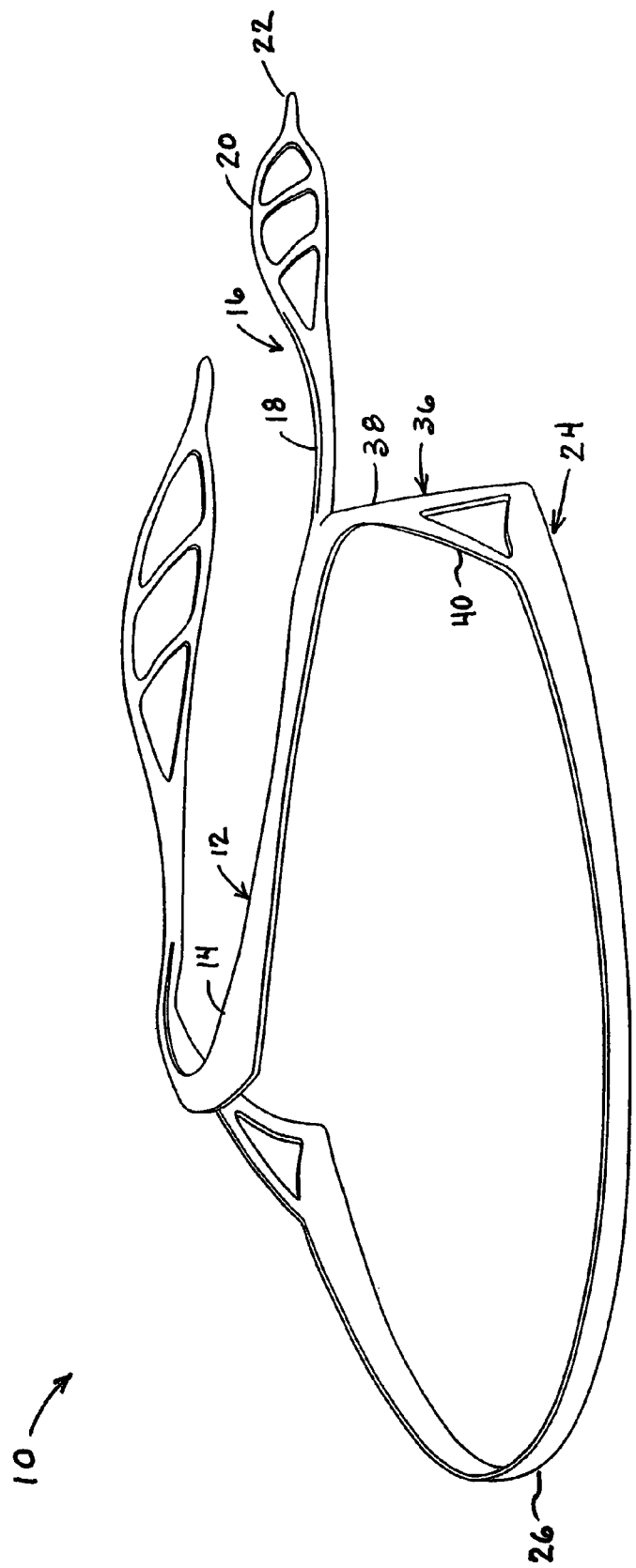
FIG. 3 is a perspective view of the face shield of FIG. 1 shown for clarity without the transparent shield or minishield attached.
Figure 4:
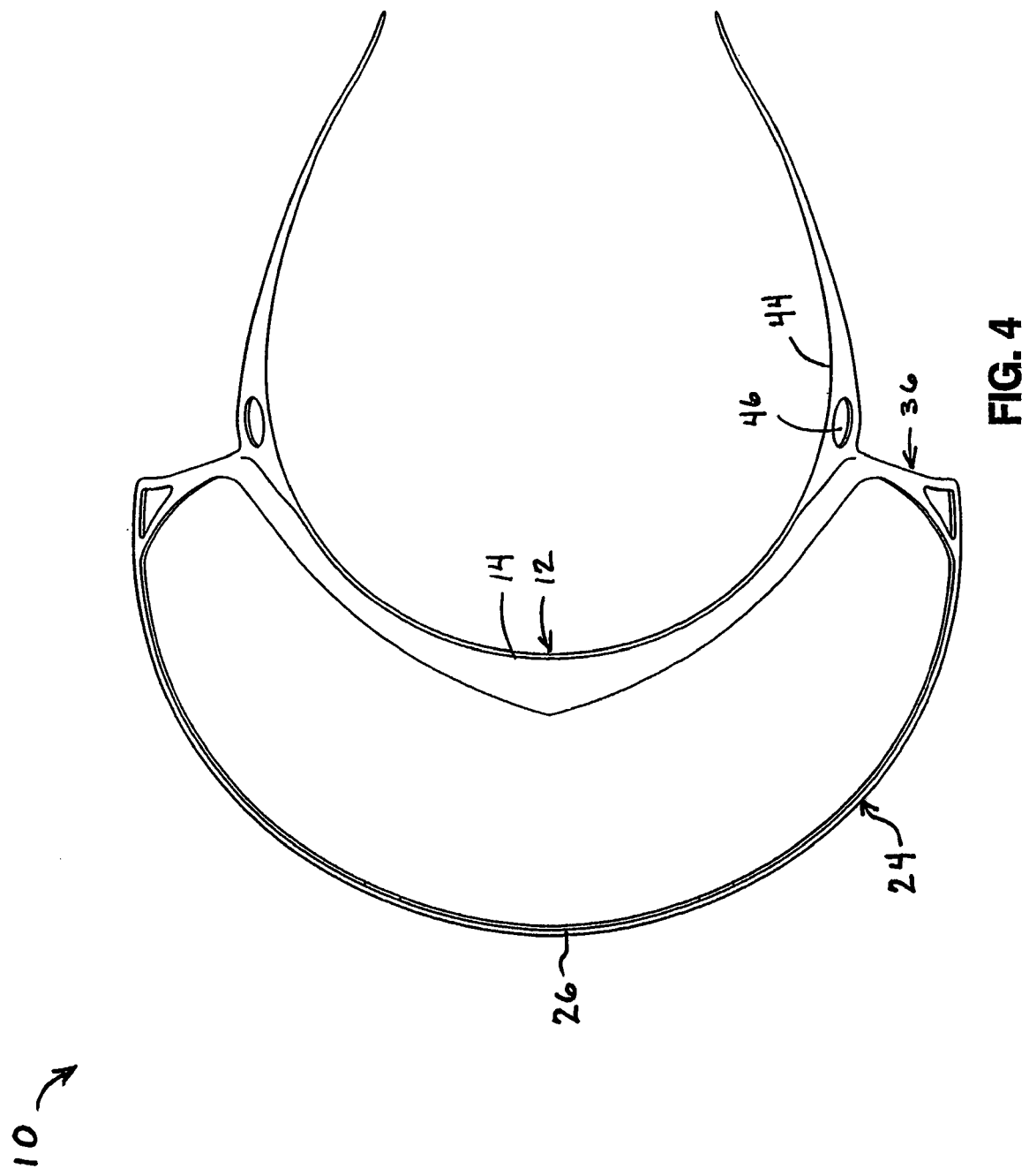
FIG. 4 is a top view of the face shield of FIG. 3.
Figure 5:
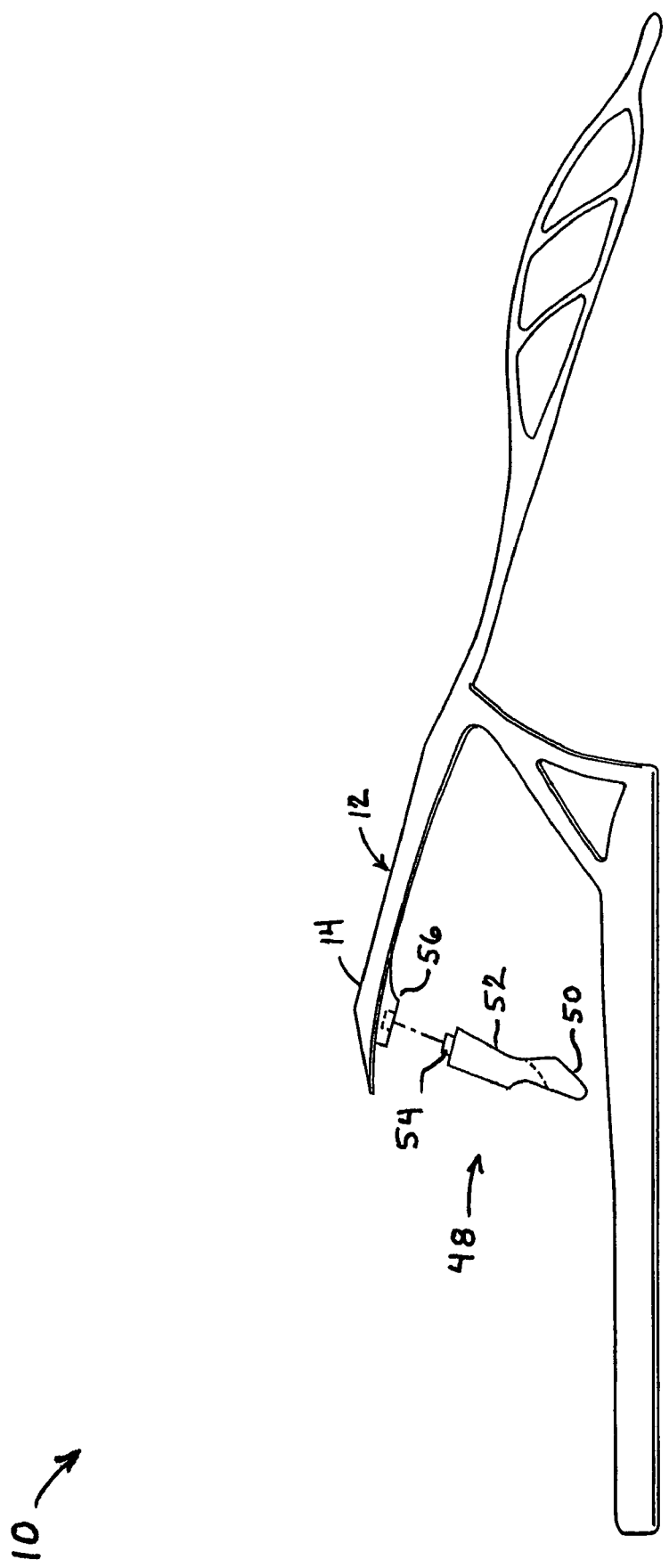
FIG. 5 is a exploded side view of the face shield of FIG. 4, shown with optional nose bridge member prior to be joined to the retention frame.

FIG. 3 through FIG. 5 illustrates the face shield framing with the transparent shield and minishield removed from the structure for the sake of clarity. Retention frame 12 depicting taper 44 is shown in FIG. 4 of support arm 16 for providing sufficient pressure along support arms 16 to securely retain the face shield on the head of the wearer. It should be noted that in order to provide sufficient tension force with reduced material, the proximal regions of support arms 16, nearing inclined support 36, are preferably formed to have a horizontal width of material that is greater than the vertical depth of material. The widened section of support arm 16 is shown with optional apertures 46, that can provide a decorative element while moderating the amount of compliance within the support arms.

An optional nose bridge member 48 is shown in FIG. 5 with curving bridge 50, vertical support 52, upper end 54, and which is preferably adapted for engagement within a retention structure 56 of the retention frame member 12. By way of example and not of limitation, engagement structure 56 may comprise a snap socket engagement mechanism (shown) configured to engage upper portion 50 of nose bridge 48. Alternatively, a narrowing slot may be utilized to engage a flange on the upper portion of the nose bridge. It should be appreciated that nose bridge 48 may be alternatively attached by any convenient method, including the use of mechanical retention, fasteners, adhesives, and so forth. The use of nose bridge member 48 can improve face shield retention and positioning as a portion of the load of face shield 10 is supported upon the nose bridge of the wearer. Nose bridge member 48, therefore, is either permanently joined or selectively joined, as a user selected face shield option, to the center of the retention frame member extending downwardly from retention frame 12. The lower portion 50 of nose bridge member 48 comprises a curving section configured for engaging the curving surface on the bridge of the nose of said wearer. The interior of the curve on nose bridge 48 may be configured with one or more pads with a view toward increasing user comfort. It should be appreciated that utilizing a nose bridge can be particularly beneficial if other equipment or elements are coupled to the face shield or frame which increase the weight being supported on the head, for example attaching an examination light, or other equipment to the face shield.

Figure 6:
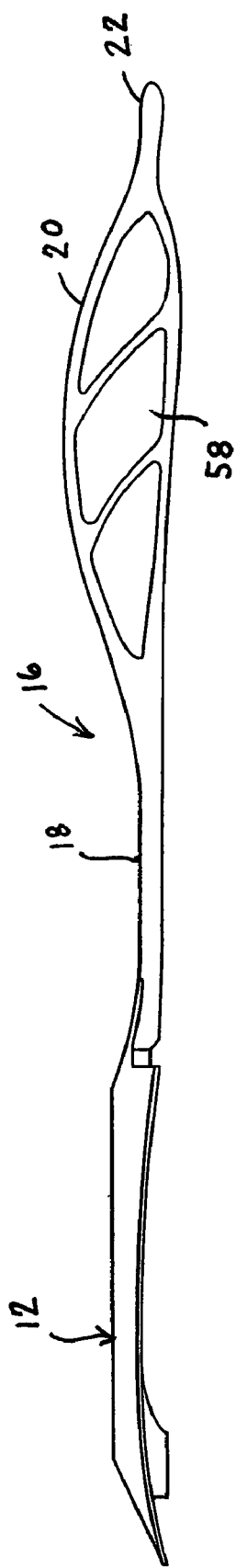
FIG. 6 through FIG. 9 are side views of support arm configurations according to aspects of the present invention.

FIG. 6 through FIG. 9 depict support arms 16 having a number of configurations within distributed contact sections 20. FIG. 6 illustrates an open web configuration 58 with narrow contact regions, which is a preferred embodiment of the support arms. It should be appreciated that the use of narrow contact regions disbursed over portions of the wearers' head are generally less subject to sliding or other frame movement in relation to broadly distributing the contact forces. Preferably a webbed portion of the distal end of the support arms comprises a perimeter that surrounds a section which includes a plurality of open regions, such as having an area of at least one quarter square inch (¼ sq. inch), or more preferably having at least one open area of at least one half square inch (½ sq. inch)

Figure 7:
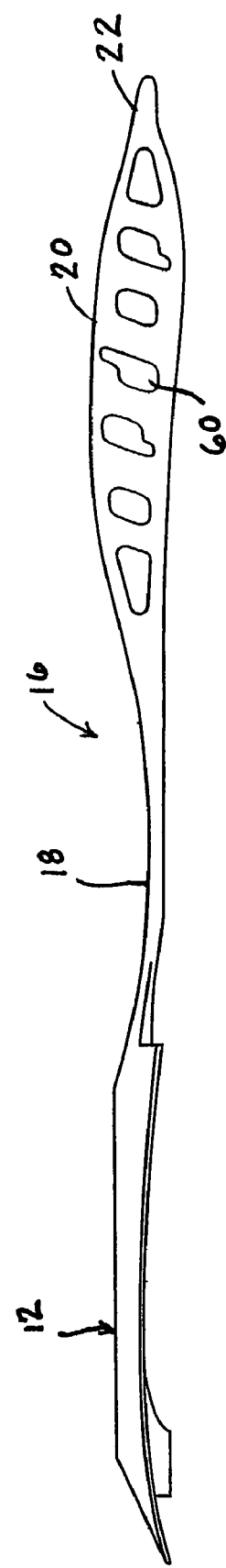
Figure 8:
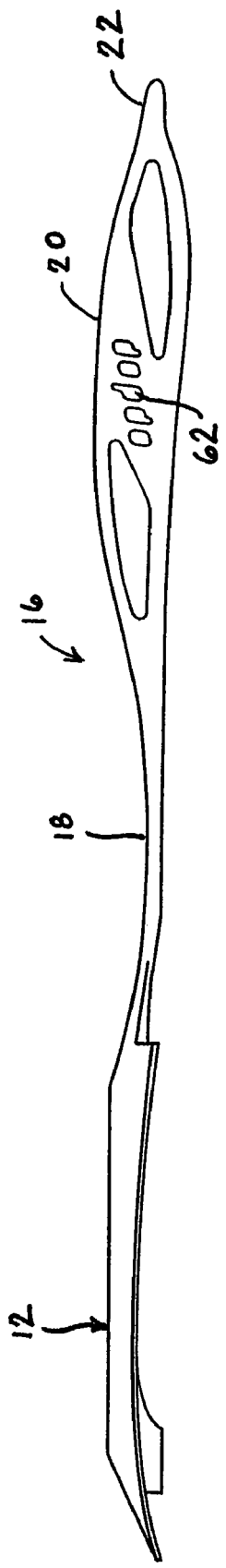
Figure 9:
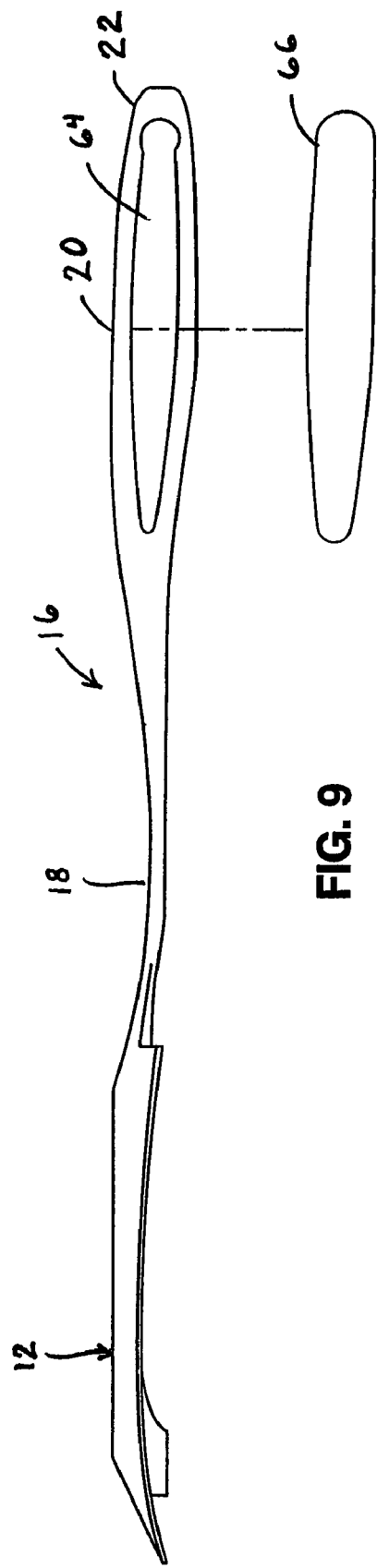

A number of other support arm configurations are depicted in the following figures. FIG. 7 illustrates a logo webbing configuration 60. FIG. 8 illustrates a combination open webbing with logo configuration 62. FIG. 9 illustrates a slot configuration 64, into which, for example, a flow cell 66 may be inserted to equalize the pressure applied by support arm 16 against the irregular surface of the head.

Optionally, materials may be applied to the interior of the face shield where it contacts the head of the wearer. For example, compressible materials such as padding, closed or open cell foam, or the like could be used.

Figure 10:
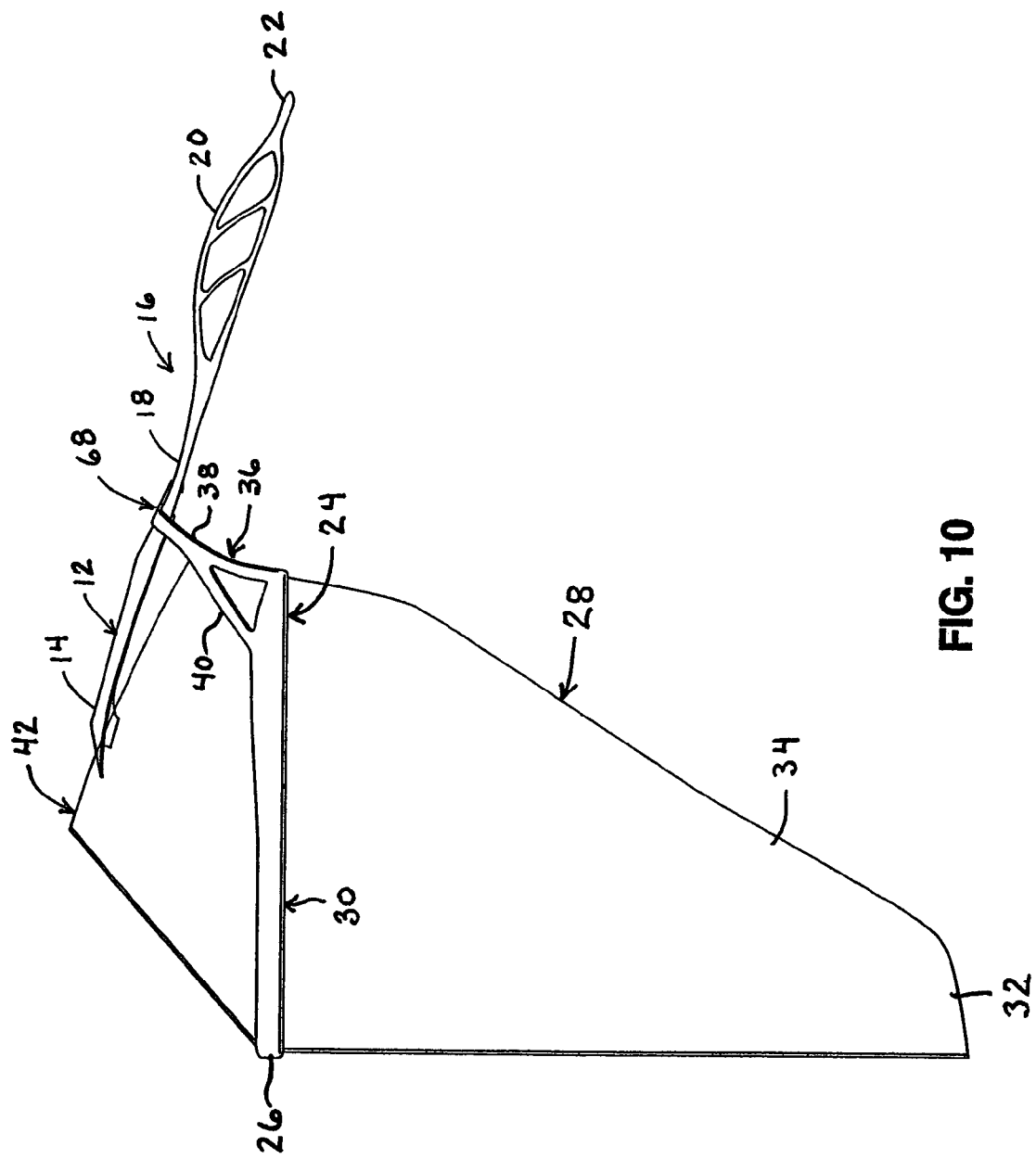
FIG. 10 is a side view of a two piece face shield, wherein the retention frame is attached prior to use to an inclined support connecting to the shield frame member.

FIG. 10 exemplifies a two piece face shield, wherein the retention frame is attached prior to use to an inclined support connecting to the shield frame member. A retention structure 68 is shown in the upper ends of the inclined support for engaging a mating structure of retention frame member 12. It should be appreciated, however, that the face shield 10 may be configured to provide separation between any one or more of the elements to facilitate storage without departing from the teachings of the present invention.

Packaging and storage space for the face shields may be reduced by configuring the face shields as separate elements that are connected to the frame elements prior to use, such as by the interlocking of engagement structures to effect mechanical joining. The face shield preferably comprises at least two separable elements. By way of example, a first portion comprises a retention frame member which may be joined to a separate element comprising the transparent shield attached to the shield frame member which is attached to the inclined support members. The transparent shield may be factory joined to the shield frame member 24, or may be semi-permanently, or temporarily joined, such as by an end-user in preparation for use. It should be appreciated, however, that the face shield may be separated into more than two elements, and that alternative groupings may be provided without departing from the teachings of the present invention. For example, the inclined support member may be alternatively permanently connected, such as to the support frame member or configured as a separate element for being joined between the support frame member and shield frame member.

Figure 11:
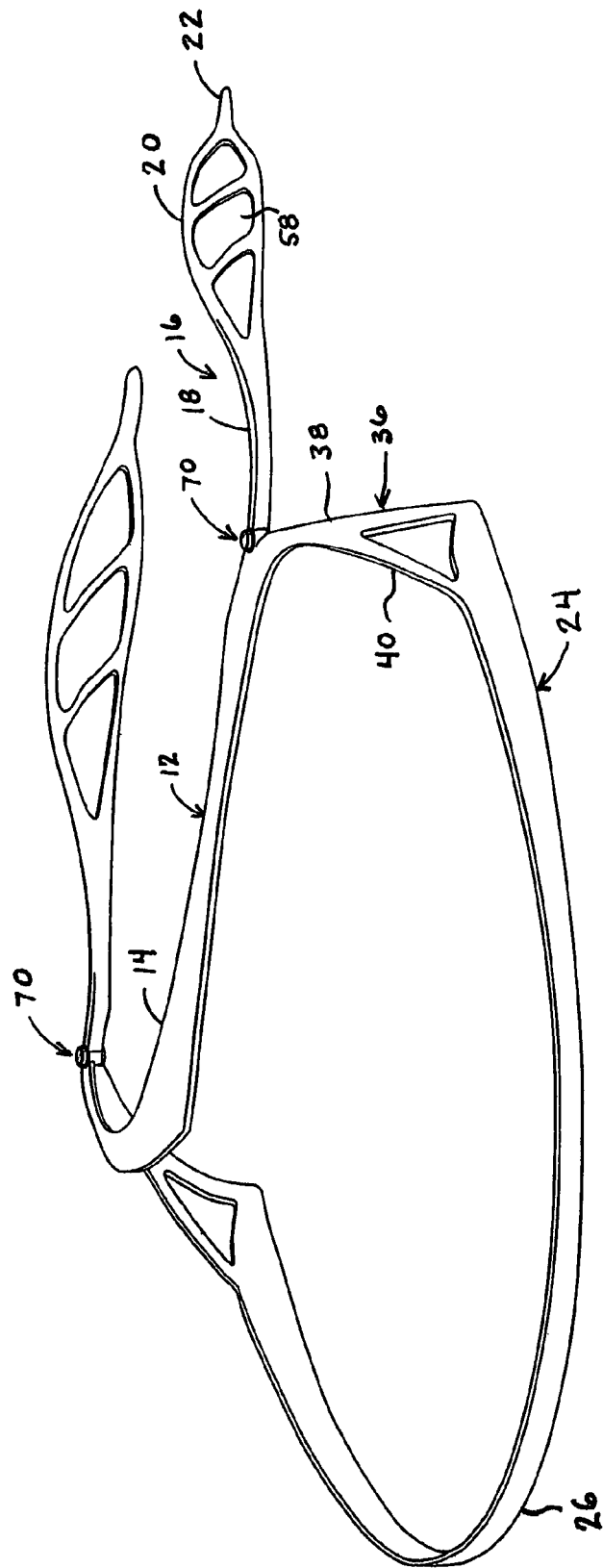
FIG. 11 is a perspective view of a face shield frame shown with locking hinges according to another embodiment of the present invention.

FIG. 11 exemplifies a face shield frame which incorporates locking hinge assemblies 70 for adjusting the contact pressure supplied by support arms 16. The hinges may be disengaged to allow adjusting the positioning of the support arms for secure retention and a comfortable fit. Although a number of support arm articulation mechanisms may be utilized, the preferred mechanisms are locking hinges as described in U.S. Pat. Nos. 6,278,788 and 6,016,808 both of which are incorporated herein by reference.

Figure 12:
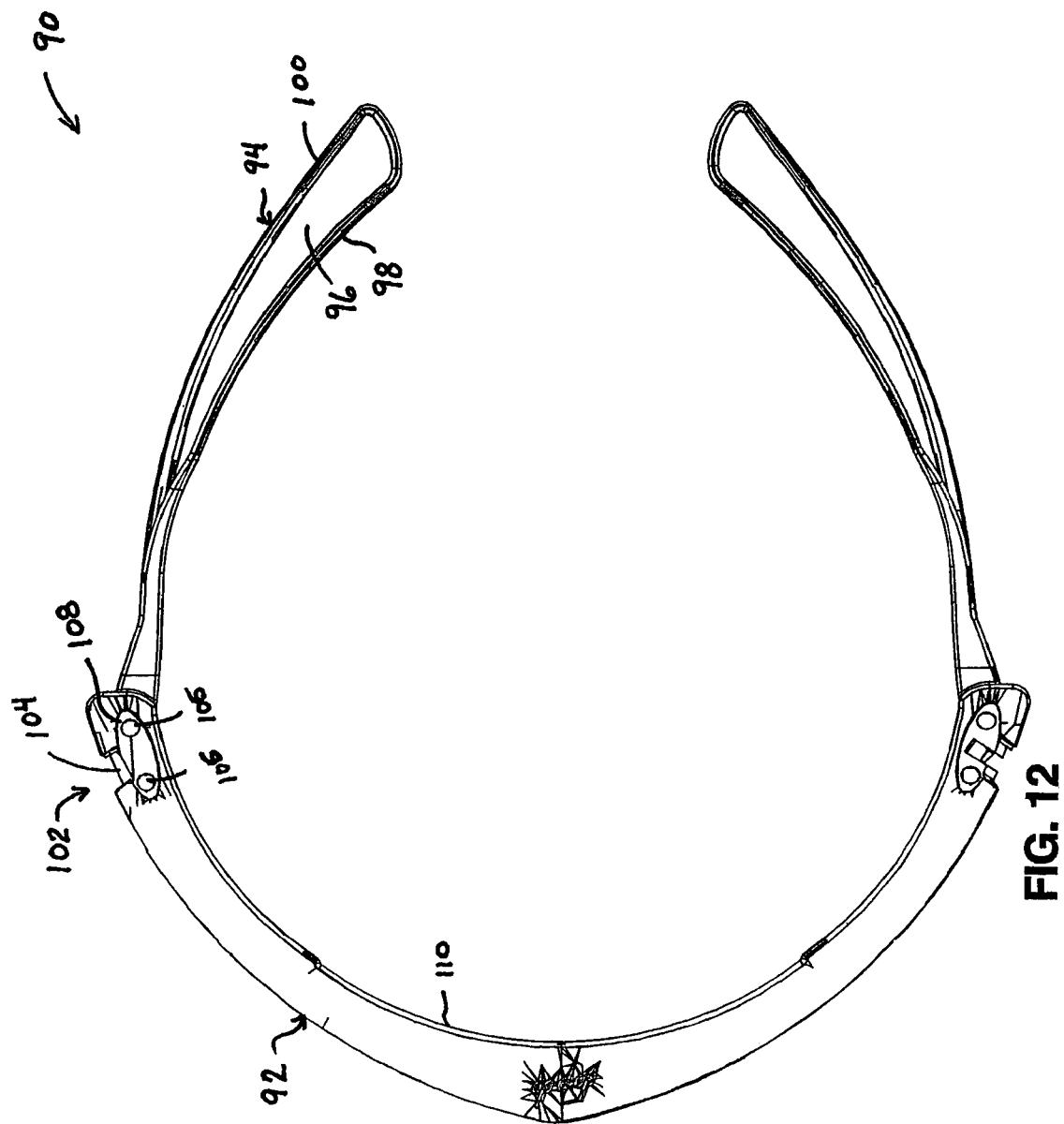
FIG. 12 is a top view of a retention frame member according to another embodiment of the present invention, shown configured for attachment of a shield frame member.
Figure 13:
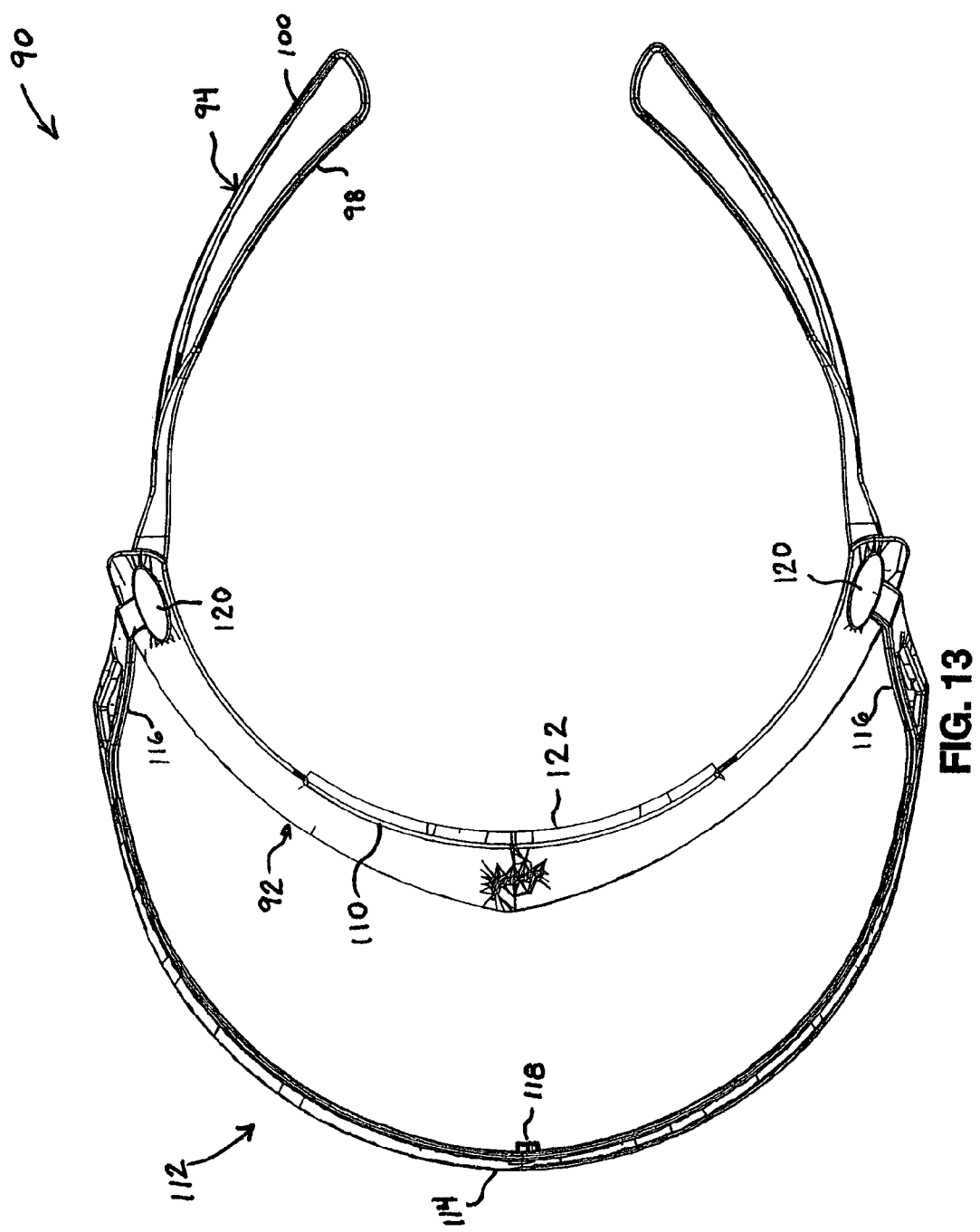
FIG. 13 is a top view of the retention member of FIG. 12, joined to a face shield frame according to an aspect of the present invention.
Figure 14:
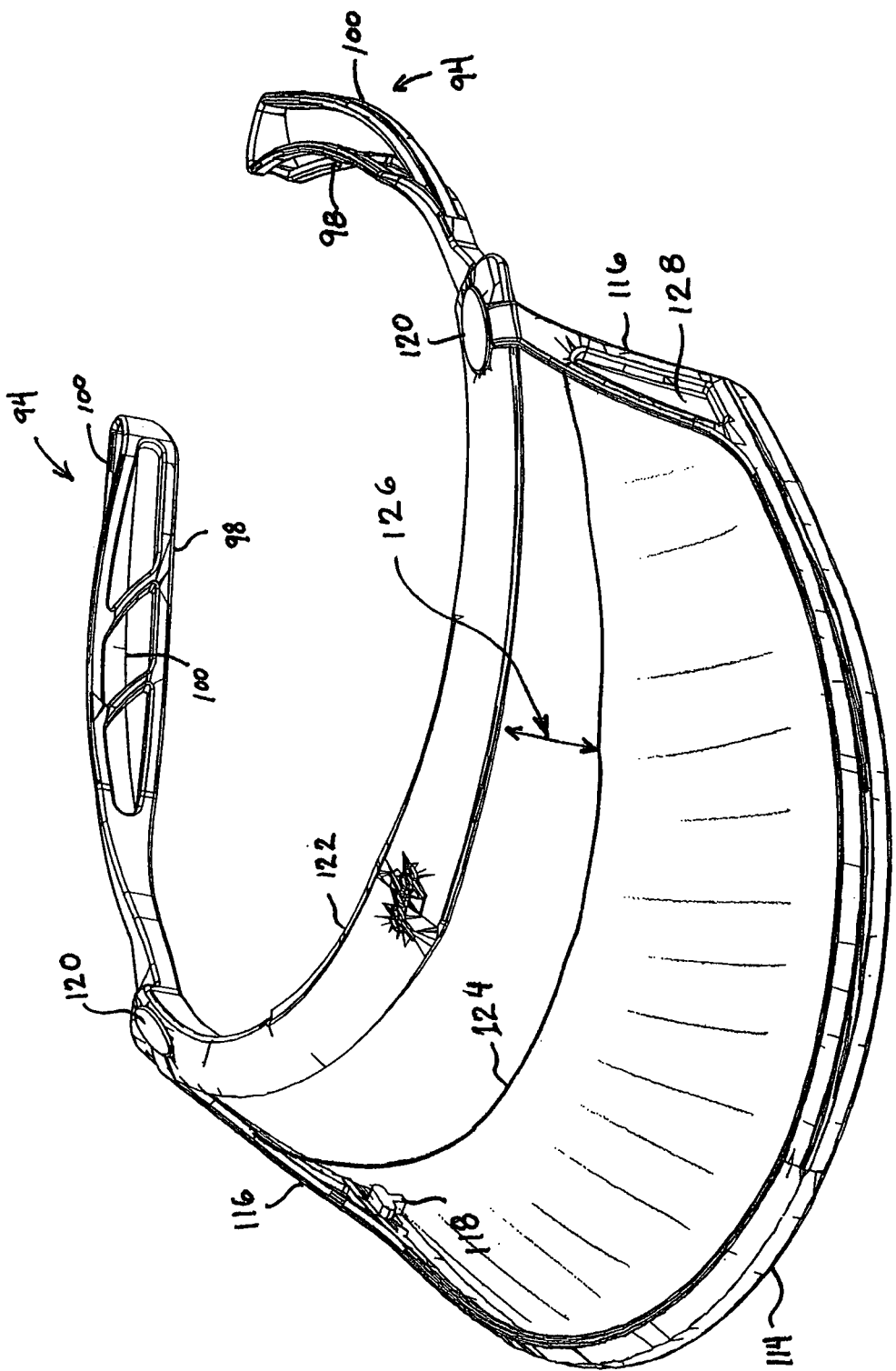
FIG. 14 is a perspective view of face shield of FIG. 13 with attached minishield.
Figure 15:
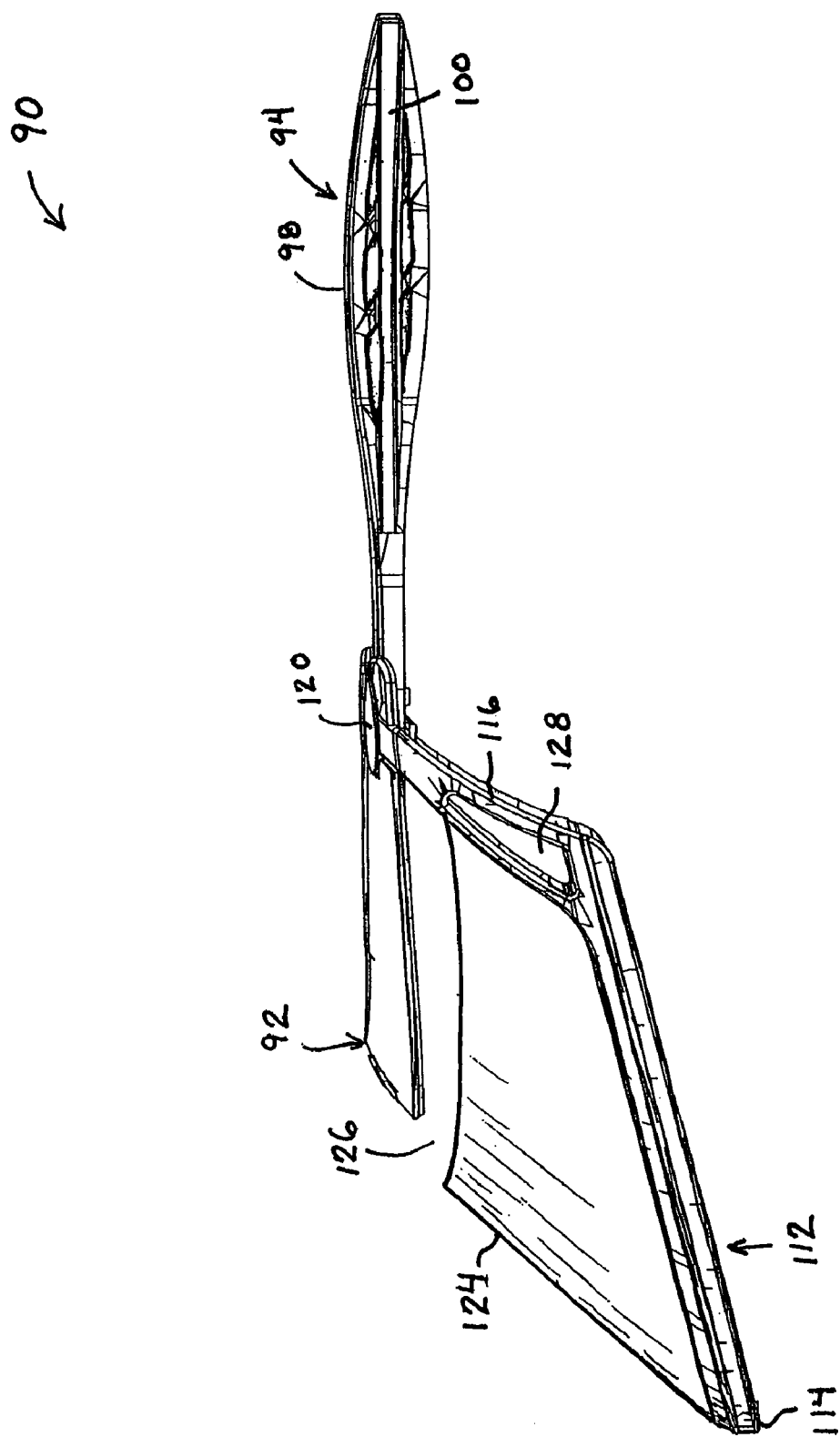
FIG. 15 is a side view of the face shield of FIG. 14.

FIG. 12 through FIG. 15 illustrate another embodiment 90 of face shield shown preferably configured with a separable shield frame member and trampoline style support arms. FIG. 12 depicts a retention frame shown for clarity without the shield frame support, while FIG. 14 and FIG. 15 depict an attached minishield member but does not show the attachment of a transparent shield.

In FIG. 12, a retention frame member 92 is shown having a central arcuate section, from which support arms 94 extend rearwardly. The device is shown configured with ventilated support arms 94, surrounding at least one opening 96. The ventilated support arms are preferably configured in a trampoline configuration having a three-dimensional webbed structure. It should be appreciated that a three-dimensional trampoline web structure provides advantages for both support and ventilation while reducing material requirements. The three-dimensional structure for support arms 94 comprises narrow compliant contact regions on the inside 98 of support arms 94 to make secure contact with the head of the wearer while exterior rigid structures 100 support the compliant webbed material 98 on the inside. It will be appreciated that the compliant regions 98 and rigid structures 100 may be formed of the same material, such as within the same mold, but with different shapes and structural cross sections.

A connection 102 provides a means of interconnecting a shield frame to the retention frame 92. A recess 104 is shown with apertures 106 for receiving connection pins. It should be appreciated that connection 102 may be implemented utilizing any desired means of connecting retention frame 92 with a shield frame member. For example a taper fit connection may be utilized, or alternatives such as post with barbs, snap-fit, and so forth.

The center arcuate section of retention frame 92 may also be configured with removable support arms 94 that may join with retention frame 92 at the same location as the support frame is joined. For example, the oval section 108 may depict a male connection of the end of a support arm 94 into a matching female receptacle within retention frame 92. The shield support frame then interconnects to the support arms which are locked to the retention frame. It will be appreciated that a number of alternative means for attaching a shield frame element exist. The shield frame connection 102, and optional support arm connection 108 are shown collocated at the position shown, by way of example and not of limitation, therefore it will be appreciated that these connections may be located along any portion of the retention frame.

A recess 110 is shown in the forward inner portion of retention frame 92 into which a cushion, such as a foam strip, or other form of forehead interfacing element, may be joined.

In FIG. 13, shield frame element 112 is shown attached forward of the center of retention frame 92 at connection 104. Retention frame 92 provides for retaining a transparent shield element (not shown) away from the face of the wearer, and preferably ventilation between the transparent shield and retention frame 92. The shield frame element 112 preferably comprises an arcuate lower edge 114 with inclined support members (drop arms) 116. A means for attaching at least one transparent shield is shown exemplified as at least one attach pin 118, which may also be referred to as a snap pin. The edges of the transparent shield connect to inclined support members 116, which are shown terminating in retention ovals 120 engaging recesses 108 within retention frame 92. A forehead interface member is depicted as a strip of foam 122 attached within recess 110 of retention frame 92. It will be appreciated that the shield frame 90 is preferably held in place on the head of the wearer largely in response to forces applied at the forehead and behind the ears by the ends of the support arms 94. Retention frame 92 is shown configured with an inner shape that is preferably relieved in regions between the ear and forehead, which results in increased comfort because circulation is not impeded in that vascular region.

FIG. 14 and FIG. 15 depicts a face shield frame 90 with minishield member 124 retained by attach pins 118 (not shown in FIG. 14, 15) and preferably engaged with inclined support members 116 on shield frame member 114. Attachment pins are preferably located in at least three locations along the periphery of shield frame member 114. The attachment of minishield 124 to a separate shield frame 114 provides beneficial ventilation space 126, which is preferably unobstructed, through which humid air rising from the wearers face can exit the face shield.

Inclined support members 116 are shown bifurcated and surrounding open area 128, which increases support without unduly increasing material weight. Design elements, logos and indicia may be additionally or alternatively included within the area depicted as open area 128.

The elements of the face shield may be fabricated in any convenient process and material, with the use of thermoplastic materials and a molding process being generally preferred.

Accordingly, it will be seen that this invention provides for the manufacture of a lightweight face shield device providing distributed retention pressure and ventilation between the transparent shield and the face of the wearer, as well as between the frame members and the head. An embodiment of the present invention has been depicted by way of example, with a few contemplated variations and options. It should be appreciated, however, that elements of the invention such as the shape or structure of the frames and support arms and so forth, may be implemented in a number of alternative ways by one of ordinary skill in the art without departing from the teachings of the present invention.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A face shield, comprising:
   a first frame member;
   support arms extending rearwardly from said first frame member;
   wherein at least a portion of said support arms are adapted with a webbed portion to distribute retention pressure on the sides of the head of a wearer of said face shield; and
   a second frame member retained forward of and below said first frame member;
   wherein said support arms are configured for being secured to the head of a wearer;
   wherein a portion of said second frame member is disposed away from the head and face of the wearer and adapted for retaining a transparent shield in a position for protecting the face of the wearer and separated from the face of a wearer; and
   wherein said second frame member is positioned forward of and below said first frame member relative to the head of a wearer when the face shield is positioned over the face of a wearer.

2. A face shield as recited in claim 1, wherein said first frame member comprises a central arcuate section from which said support arms extend.

3. A face shield as recited in claim 2, further comprising an articulating mechanism within at least one of said support arms to provide adjustability of said face shield for different head sizes and shapes.

4. A face shield as recited in claim 3, wherein said articulating mechanism comprises a locking hinge assembly.

5. A face shield as recited in claim 4, wherein said locking hinge assembly incorporates a push button for disengaging a lock wherein a position of said support arm may be adjusted.

6. A face shield as recited in claim 1, further comprising inclined support members connecting said first frame member in a tiered arrangement separated above said second frame member.

7. A face shield as recited in claim 1, further comprising a transparent shield member joined to, and extending downwardly from, said second frame member.

8. A face shield as recited in claim 7, wherein said transparent shield member comprises a substantially transparent polymeric material.

9. A face shield as recited in claim 8, wherein said transparent shield member comprises a section of material removed from a sheet of transparent polymeric material.

10. A face shield as recited in claim 8, wherein said transparent polymeric material is selected from the group of polymeric materials consisting of polystyrene, acrylic, polyethylene, terephthalate, polycarbonate, or equivalent polymeric material.

11. A face shield as recited in claim 1, wherein said first frame member is adapted for positioning on the head of a wearer at an angle with the front of said first frame member raised above the distal end of said support arms.

12. A face shield as recited in claim 1, further comprising an engagement structure within said first frame member into which a removable nose bridge member can be received for supporting said face shield.

13. A face shield as recited in claim 1, wherein said webbed portion comprises a perimeter that surrounds a section which includes a plurality of open regions.

14. A face shield as recited in claim 13, wherein at least one of said open regions is at least one quarter square inch in size.

15. A face shield as recited in claim 13, wherein at least one of said open regions is at least one half square inch in size.

16. A face shield as recited in claim 1, wherein an arc of curvature of said second frame member has a radius which exceeds that of said first frame member.

17. A face shield as recited in claim 16, wherein said arc of curvature of said second frame member has a radius which exceeds that of said first frame member by a minimum of approximately one half inch.

18. A face shield as recited in claim 16, wherein said arc of curvature of said second frame member has a radius which exceeds that of said first frame member by approximately three quarters of an inch to approximately three inches.

19. A face shield as recited in claim 1, further comprising:
   a minishield adapted for attachment to said second frame member in a position from said second frame member toward the top of the head of an intended wearer;
   wherein said second frame member is configured for retaining said minishield.

20. A face shield as recited in claim 19, wherein said minishield comprises a shading material through which light transmission is limited.

21. A face shield as recited in claim 20, wherein said shading material comprises a semi-transparent to opaque material.

22. A face shield as recited in claim 1, further comprising a locking hinge assembly within at least one of said support arms configured for allowing adjustment of the angular relationship between said support arms.

23. A face shield as recited in claim 22, wherein said locking hinge assembly incorporates a push button for disengaging the lock wherein said support arm may be repositioned.

24. A face shield as recited in claim 1, wherein the material of said first frame member, said second frame member, and said inclined support member comprises a thermoplastic material.

25. A face shield as recited in claim 1, further comprising a nose bridge member joining to and extending downwardly from said first frame member.

26. A face shield as recited in claim 25, wherein said first frame member is adapted for receiving and retaining said nose bridge.

27. A face shield as recited in claim 25, wherein said nose bridge member comprises:
a vertical support; and
a curving support adapted for engaging the curving surface on the bridge of the nose of said wearer.

28. A face shield as recited in claim 1, wherein said first frame member is adapted with an engagement structure for receiving a removable nose bridge member for supporting said face shield.

29. A face shield as recited in claim 28, wherein said engagement structure comprises a slot or channel into which a mating portion of said nose bridge is engaged for retention.

30. A face shield as recited in claim 1, wherein said second frame member is configured for being removably joined to said first frame member.

31. A face shield as recited in claim 30, wherein said second frame member and said first frame member are configured with interlocking engagement structures for mechanically joining said second frame member and said first frame member.

32. A face shield for protecting the face of a wearer from contact with flying debris or biological hazards, comprising:
a first frame member;
an engagement structure within said first frame member into which a removable nose bridge member can be received for supporting said face shield;
support arms extending rearwardly from said first frame member;
a second frame member;
an inclined support member connecting said first frame member in a tiered arrangement above and behind said second frame member; and
a transparent shield member coupled to and extending from said second frame member for protecting the face of the wearer and retained in separation from the head and face of the wearer;
wherein said support arms are configured for being secured to the head of a wearer; and
wherein said second frame member is positioned forward of and below said first frame member relative to the head of a wearer when the face shield is positioned on the head of a wearer.

33. A face shield as recited in claim 32, further comprising a distributed contact area on said support arms which are adapted for applying retention pressure on the sides of the head of a wearer.

34. A face shield as recited in claim 3, wherein said first frame member has a substantially arcuate center section configured for positioning on a forward portion of the head of a wearer of said face shield.

35. A face shield as recited in claim 32:
wherein said second frame member has a substantially arcuate shape;
wherein said second frame member connecting to said first frame member circumscribes an opening.

36. A face shield as recited in claim 35, wherein the centers of said second frame member and said first frame member are separated by at least one inch.

37. A face shield as recited in claim 32, further comprising enlarged contact areas on said support arms, having a substantially larger width of material than said support arm, configured for applying retention pressure on the sides of the head of a wearer.

38. A face shield as recited in claim 32:
wherein said support arms comprise articulated support arms connected to said first frame member configured for adjusting the retention pressure applied between said articulated support arms and the head of a wearer of said face shield.

39. A face shield as recited in claim 38, wherein said articulated support arms comprise position lockable hinge assemblies connecting said support arms to said first frame member.

40. A face shield as recited in claim 32, wherein said engagement structure comprises a slot or channel into which a mating portion of said nose bridge is engaged for retention.

* * * * *